United States Patent [19]

Seno

[11] Patent Number: 5,075,100
[45] Date of Patent: Dec. 24, 1991

[54] IRON COLLOID-LABELED ANTIBODY, PREPARATION THEREOF AND HISTOCHEMICAL DETECTION THEREBY

[75] Inventor: Satimaru Seno, Okayama, Japan

[73] Assignee: Wako Pure Chemical Industries, Ltd., Osaka, Japan

[21] Appl. No.: 242,731

[22] Filed: Sep. 9, 1988

[30] Foreign Application Priority Data

Sep. 30, 1987 [JP] Japan ................................. 62-246834

[51] Int. Cl.⁵ ........................ G01N 1/30; G01N 33/48
[52] U.S. Cl. .......................................... 424/3; 435/7.1; 435/7.21; 436/501; 436/547; 436/548; 530/387; 530/388
[58] Field of Search ............... 436/501, 529, 524, 527, 436/530, 532, 510; 435/7, 4, 5; 530/810, 821

[56] References Cited

U.S. PATENT DOCUMENTS 4,252,562  6/1988  DeBrabunder et al. ............... 435/29

OTHER PUBLICATIONS

Pares et al., Gold labelled Antibody Decoration in Diagnosis of Plant Virus by Immuno-Electro Microscopy, Journal of Immun. Methods, 51(1982) 23–28.
Moeremans et al., Ferr: Bye: Colloidal Iron Binding . . . for Staining of Proteins . . . Analytical Biochemistry 153, 18–22 (1986).
S. Seno et al., Catoionic Cacodylate Iron Colloid for Detection of Anionic Sites on Cell Surface and the Histochemical Stain of Acid Mucopolysaccharides, Histochemistry (1983) 78:27–31.
S. Seno et al., Fine-granular Cationic Iron Colloid—Its Preparation, Physicochemical Characteristics and Histochemical Use for the Detection of Ionized Anionic Groups, Histochemistry (1985) 82:307–312.

*Primary Examiner*—Sam Rosen
*Attorney, Agent, or Firm*—David G. Conlin; Linda M. Buckley

[57] ABSTRACT

Disclosed is an iron colloid-labeled antibody wherein an iron colloid is bound to IgG or an antigen binding fragment thereof without a loss of antibody specificity. An iron colloid stabilized with cacodylic acid or the salt thereof (ferric cacodylate colloid) is preferable.

This iron colloid-labeled antibody is prepared by mixing the iron colloid stabilized with cacodylic acid or the salt thereof with IgG or the antigen binding fragment thereof at a pH of about 7.4 to 7.5.

The iron colloid-labeled antibody is used for the histochemical detection of specific constituents of cells or tissued under both a light microscope and an electron microscope, which gives distinct stained figures in each case.

6 Claims, No Drawings

IRON COLLOID-LABELED ANTIBODY, PREPARATION THEREOF AND HISTOCHEMICAL DETECTION THEREBY

BACKGROUND OF THE INVENTION (a) Field of the Invention

The present invention relates to a novel and useful iron colloid-labeled antibody which is used for the histochemical detection of specific constituents of cells or tissues under a light microscope and an electron microscope in medical or biological experiments.

(b) Description of the Prior Art

As the labeled antibody for the histochemical detection of specific substances present in tissues or cells, and constituents of tissues or cells, there have been known and generally widely used the fluorescent antibody, the peroxidase-labeled antibody, the ferritin antibody, the gold colloid-labeled antibody and the like.

Of the histochemical detecting methods wherein these various labeled antibodies are used, the fluorescent antibody method was developed for ultraviolet microscopy, which can not be utilized for general light microscopy and electron microscopy and gives only indistinct images. The peroxidase-labeled antibody method (PAP method) is very excellent and widely used for light microscopy and electron microscopy now. However, the specimens post stained with osmic acid, uranium acetate, lead citrate or the like are liable to show unclear existence of the reaction products, because of diffuse appearance of the reaction products under an electron microscope. In respect to this point, the staining by the ferritin antibody method or the gold colloid-labeled antibody method provides very distinct electron microscopic images. However, these methods are difficult to expect distinct light microscopic images and have the disadvantage that the tissue permeability of the labeled antibody is remarkably poor because the labeled antibody is large in size.

SUMMARY OF THE INVENTION

Under the background described above, the present invention was completed. It is a primary object of the present invention to provide a novel and useful labeled antibody which can be used for light microscopy and electron microscopy in the histochemical detecting methods wherein labeled antibodies are used, has the excellent tissue permeability, and provides distinct stained images in each case.

In order to achieve the object described above, the present inventor has diligently studied various labeled antibodies. As a result, it was found that an iron colloid-labeled antibody prepared by binding an iron colloid as a labeling material to IgG, an antibody protein, or to an antigen binding fragment thereof [namely, Fab, Fab' and F(ab')2 ] was able to achieve the object and was exceedingly useful, thus arriving at the present invention.

In accordance with the present invention, there are provided an iron colloid-labeled antibody wherein an iron colloid is bound to IgG which is an antibody protein or to an antigen binding fragment thereof, without a loss of antibody specificity; a process for preparing an iron colloid-labeled antibody which comprises mixing an iron colloid stabilized with cacodylic acid or a salt thereof (ferric cacodylate colloid) with IgG or an antigen binding fragment thereof at a pH of about 7.4 to about 7.5, i.e., higher pH than pI of IgG; and a histochemical detecting method wherein the detection is carried out by a tissue antigen staining method by use of a labeled antibody, which comprises using an iron colloid-labeled antibody as the labeled antibody.

DESCRIPTION OF THE PREFERRED EMBODIMENTS

Usually, the iron colloid-labeled antibody of the present invention can be easily obtained in the following manner:

A so-called ferric cacodylate colloid (hereinafter referred to as FeCac for brevity) stabilized with cacodylic acid or the salt thereof is usually used as an iron colloid.

This colloid is mixed with IgG, the antibody protein, or the antigen binding fragment thereof [namely, Fab, Fab' and F(ab')2]at a pH of about 7.4 to about 7.5. Consequently, FeCac is easily bound to IgG or the antigen binding fragment thereof to produce the FeCac-labeled antibody. Although FeCac is usually used in excess to IgG or the antigen binding fragment thereof, unreacted FeCac is removed by adsorption with a column chromatography in which a cation exchanger resin is used. After unreacted FeCac is removed, the reaction solution (FeCac-labeled antibody solution) is condensed by an ultrafilter. Thus, the FeCac-labeled antibody is isolated successfully.

FeCac may be prepared according to the methods described in the literatures such as Histochemistry (1983) 78:27–31 and Histochemistry (1985) 82:307–312, for example, by adding 1 volume of a 0.1M FeCl solution to 9 volumes of boiling distilled water with stirring, cooling to room temperature and then adding 5 volumes of a 0.1M cacodylic acid buffer solution (pH 7.3 to 7.4) thereto, or by adding 9 volumes of a 0.1M ammonium cacodylate solution (which is prepared by adding aqueous ammonia to a 0.1M cacodylic acid solution to adjust the pH to 7.3) to 1 volume of a 0.1M FeCl$_3$ solution, boiling the mixture until the color turns to red-brown, cooling to room temperature and then diluting suitably with the ammonium cacodylate solution.

The iron colloid-labeled antibody of the present invention is particularly desirable to be prepared using an iron colloid stabilized with cacodylic acid or the salt thereof, but may be prepared using an iron colloid similarly stabilized with an organic acid such as citric acid, acetic acid, lactic acid or propionic acid, the salt thereof, an amino acid such as asparagine, aspartic acid or histidine, the salt thereof or the like, instead of cacodylic acid, though some intermediate like Protein A is required.

The salts include the alkali metal salts such as sodium salts and potassium salts; the ammonium salts; and the alkali earth metal salts such as calcium salts and magnesium salts, which are usually used.

The bonding in the FeCac-labeled antibody of the present invention is highly stable, and the antibody reacts specifically with a corresponding antigen of a fixed tissue. Namely, the binding of FeCac to the antibody does not get rid of a property as a specific antibody from the FeCac-labeled antibody When tissues or cells are stained with the iron colloid-labeled antibody of the present invention, the localization of target substances such as target antigens can be very clearly found on the tissues or cells by the Prussian Blue reaction post-stained with Nuclear fast red under a light microscope, and by the specific figure of the electron opaque iron colloid particles under an electron microscope. In case of light microscopy, for example, formalin fixed paraffin sections are deparaffinized, reacted with the iron colloid-labeled antibody solution of the present invention at 4° C. overnight, then washed to remove the excess antibody, fixed the antibody with formalin, followed by the Prussian blue reaction and post-stained with Nuclear fast red. Thus, the antigen of the tissues is stained deep blue In case of electron microscopy, for example, tissues fixed with a Zamboni's fixative are cut into 60 to 100 μm-thick sections by a vibratome and stained with the iron colloid-labeled antibody of the present invention, fixed with glutaraldehyde, embedded in Epon and ultra thin sections are made according to the conventional method. Consequently, the iron colloid particles localized in the site of the antigen of the tissues can be observed under an electron microscope.

The tissue antigen staining method using the iron colloid-labeled antibody of the present invention is simpler in operation than the PAP method. Moreover, while the PAP method and the ferritin antibody method are interfered by endogenous peroxidase and endogenous ferritin respectively, the method using the antibody of the present invention dose not have such a problem at all. Further, the tissue permeability of the antibody of the present invention is superior to that of the gold colloid-labeled antibody.

According to the tissue antigen staining method using the iron colloid-labeled antibody of the present invention, there can be selectively and very distinctly stained detecting objects, for example, various antigens such as various immunoglobulins, lymphoid cell membrane antigens, intracellular enzymes (for example, glucagon or insulin in pancreatic Langerhans' islands, or elastase in exocrine cells), carcinoembryonic antigens and viral antigens; specific proteins such as S-100 protein and neuron specific enolase (NSE), and the like. Therefore, the presence thereof, the distribution of the intracellular localization thereof and so on can be easily confirmed, and the method is extremely accurate.

The iron colloid-labeled antibody of the present invention, particularly the FeCac-labeled antibody, can also be very effectively used for western blotting.

The present invention will hereinafter be described in detail with the following Examples It is understood of course that these Examples are not intended to limit the scope of the invention.

EXAMPLE 1

One volume of a 0.1M ferric chloride solution was slowly added dropwise to 9 volumes of boiling distilled water, while taking care not to lower the temperature, to prepare an iron colloid solution. The iron colloid solution thus obtained was cooled to room temperature, and 5 volumes of a 0.1M cacodylic acid buffer solution (hereinafter referred to as CBS for brevity), pH 7.4, was added thereto. After adjusting the pH of the solution to 7.4 to 7.5 with 1 N NaOH, 1 volume of an IgG solution (25 mg/ml) was added to this solution and the mixture was thoroughly mixed by stirring. An excess of the iron colloid was removed by adsorption with a column chromatography in which Amberlite CG50 (cation exchange resin) was used. Thus, iron colloid-labeled IgG was obtained The size of the iron colloid particles was 30 to 50 Å.

EXAMPLE 2

Nine volumes of a 0.1M cacodylic acid solution was added to 1 volume of a 0.1M ferric chloride solution, and the pH of the mixture was adjusted to 7.3 with aqueous ammonia. This solution was boiled until the color turned to red-brown, and cooled to room temperature, to obtain an iron colloid solution The pH of this solution was adjusted to 7.4 to 7.5 with aqueous ammonia. The solution was then reacted with the IgG solution and an excess of the iron colloid was removed in the same manner as in Example 1 to obtain iron colloid-labeled IgG. The size of the iron colloid particles thus obtained was 5 to 10 Å.

EXAMPLE 3

Staining of Tissue Antigens With An Iron Colloid-Labeled Antibody for Light Microscopy

Operation Procedure (1) Various tissues later described (i) to (iv) were with 10% formalin solution, cut to paraffin section (4 to 6 μm in thickness) after water-washing and dehydration according to the conventional method, deparaffinized, washed twice with water and with a 0.01M phosphoric acid buffer solution (hereinafter referred to as PBS for brevity), pH 7.4, for 2 minutes.

(2) These sections were incubated with 10% normal goat serum in 0.01M PBS, pH 7.4, at 37° C. for 30 minutes and further incubated with rabbit antibodies (about 300 times) against the target antigens at 4° C. overnight.

(3) After incubation the sections were washed 3 times with a 0.1M CBS, pH 7.4, at 4° C.

(4) After washing the sections were reincubated with the FeCac-labeled goat anti-rabbit IgG antibody (diluted 30 to 60 times) prepared by the method of Example 2, for 30 to 60 minutes.

(5) After reincubation the sections were washed with the 0.1M CBS, pH 7.4, at 4° C. for 10 to 20 minutes, fixed with formalin, washed with water subjected to the Prussian blue reaction (for 5 minutes) and then thoroughly washed with distilled water.

(6) The sections thus washed were thereafter post-stained with Nuclear fast red for 5 minutes, dehydrated, penetrated and mounted to provide samples for light microscopy.

Result (i) In the sample prepared from the tissue sections of leiomyosarcoma, Desmin was positive.

(ii) In the sample prepared from the tissue sections of schwannoma, S-100 protein was positive (iii) In the sample prepared from the tissue sections of mammary cancer, carcino embryonic antigen (CEA) was positive in the portion of adenocarcinoma.

(iv) In the sample prepared from the tissue sections of malignant schwannoma, neuron specific enolase (NSE) was positive.

In all cases of (i) to (iv) described above, the stained images were clear and excellent in specificity. All stained images were extremely distinct and comparable to the staining results obtained by the conventional PAP method.

EXAMPLE 4

Staining of Tissue Antigens With An Iron Colloid-Labeled Antibody for Electron Microscopy The pig pancreas tissue section treated with FeCac-labeled rabbit anti-pig elastase antibody for electron microscopy as described below showed iron granules specifically appeared in the cavities of rough surfaced endoplasmic reticula Golgi vesicles and on the exocretory granules under an electron microscope. The operation procedure was as follows:

(1) Small pieces of fresh pig pancrease tissue were fixed with Zamboni's fixative at 4° C. for 24 hours.

(2) Sections of 60 to 100 μm in thickness were prepared using a vibratome.

(3) The sections were washed with 0.05M CBS in 0.3M sucrose solution, pH 7.4, at 4° C.

(4) After washing, the sections were incubated with 10% normal rabbit serum at room temperature for 20 minutes, followed by removal of the liquid, and then incubated with the ferric cacodylate-labeled rabbit anti-pig elastase IgG at 4° C. overnight.

(5) After incubation sections were washed with 0.05M CBS in 0.3M sucrose 3 times for 10 minutes, and then fixed with 1% glutaraldehyde solution for 15 minutes.

(6) After fixation, the fixed sections were washed with the above CBS three times for 10 minutes, and then re-fixed with 2% osmic acid solution.

(7) After dehydration the samples were embedded in Epon, ultra thin sections were prepared by the conventional method and observed under an electron microscope without staining or after staining with uranium acetate and lead citrate.

As described above, the present invention provides a novel labeled antibody to be used for the tissue antigen staining method. The iron colloid-labeled antibody of the present invention has effects of being available for both light and electron microscopy simply in procedure as compared to the conventional method and giving distinct image of target antigens in cells and tissues. The labeled antibody can also be applied for the detection of antigens in electrophoresis.

I claim:

1. An iron colloid-labeled antibody wherein an iron colloid which is stabilized with an organic acid, amino acid or a salt thereof is bound to IgG which is antibody protein or to an antigen binding fragment thereof, without a loss of antibody specificity.

2. The iron colloid-labeled antibody according to claim 1, wherein the iron colloid is one stabilized with cacodylic acid or a salt thereof (ferric cacodylate colloid).

3. A process for preparing an iron colloid-labeled antibody which comprises mixing an iron colloid stabilized with cacodylic acid or a salt thereof (ferric cacodylate colloid) with IgG or an antigen binding fragment thereof at a pH of about 7.4 to about 7.5.

4. A histochemical detecting method of a target antigen wherein the detection is carried out by staining a tissue antigen by use of a labeled antibody, which labeled antibody comprises an iron colloid-labeled antibody wherein the iron colloid is stabilized with an organic acid, amino acid or a salt thereof.

5. A histochemical detecting method according to claim 4, which is carried out for light microscopy.

6. A histochemical detecting method according to claim 4, which is carried out for electron microscopy.

* * * * *